United States Patent [19]
Suzuki et al.

[11] Patent Number: 6,071,536
[45] Date of Patent: Jun. 6, 2000

[54] GELATIN CAPSULE HAVING ADJUSTED WATER ACTIVITY

[75] Inventors: Yusuke Suzuki, Izumi; Hidekazu Syodai, Takatsuki; Chisato Nakajima, Osaka, all of Japan

[73] Assignee: Shionogi & Co., Ltd., Osaka, Japan

[21] Appl. No.: 08/913,874

[22] PCT Filed: Mar. 21, 1996

[86] PCT No.: PCT/JP96/00728

§ 371 Date: Dec. 18, 1997

§ 102(e) Date: Dec. 18, 1997

[87] PCT Pub. No.: WO96/29996

PCT Pub. Date: Oct. 3, 1996

[30] Foreign Application Priority Data

Mar. 29, 1995 [JP] Japan .................................. 7-071246

[51] Int. Cl.[7] .................................................. A61K 9/48
[52] U.S. Cl. ........................ 424/452; 424/451; 424/456; 514/772.3; 514/781; 514/962
[58] Field of Search ........................ 424/451, 452, 424/456; 514/962, 772.3, 781

[56] References Cited

U.S. PATENT DOCUMENTS

| | | | |
|---|---|---|---|
| 5,131,953 | 7/1992 | Kasica et al. | 127/65 |
| 5,393,054 | 2/1995 | Rouffer | 273/58 H |

FOREIGN PATENT DOCUMENTS

| | | |
|---|---|---|
| 61-18725 | 1/1986 | Japan . |
| 61-57522 | 3/1986 | Japan . |
| 63-174929 | 7/1988 | Japan . |

*Primary Examiner*—James M. Spear
*Attorney, Agent, or Firm*—Foley & Lardner

[57] ABSTRACT

A gelatin capsule having adjusted water activity and preserved in a closed system, which contains, packed herein, an additive(s) selected from the group consisting of carboxymethyl cellulose calcium, crosscarmellose sodium, partially gelatinized starch and polyvinyl polypyrrolidone in the proportion of 50 to 150 wt. % of the total quantity of the gelatin of the said capsule.

10 Claims, 5 Drawing Sheets

Fig. 1

Relation between temperature and water activity of gelatin

Fig. 2

(
CS : Cornstarch
MCC : Crystalline cellulose
CMC : Carboxymethyl cellulose Ca
PCS : Partially gelatinized starch
)

Fig. 5

GELATIN CAPSULE HAVING ADJUSTED WATER ACTIVITY

This application is a 371 of PCT/JP96/00728 filed Mar. 21, 1996.

TECHNICAL FIELD

The present invention relates to a gelatin capsule having an improved internal moisture stability in a closed system through the adjustment of the water activity of the content in the capsule.

BACKGROUND ART

Quality of a capsule, that is, stability of its structure, pharmacological activity of drugs as the content, and appearance thereof is closely related to the water or moisture activity. For example, it has been known that, even if a gelatin capsule was manufactured under an appropriate condition, the moisture in the capsule coating and the content drugs evaporates during preservation in a closed system, especially under heating, which possibly leads to hyper humidity condition (hyper water activity) of inside of the capsule. When a content drug comprises an active ingredient liable to change with moisture, or when moisture cannot be separated easily from an active ingredient and impurities unstable to moisture are co-exist, the content drug necessarily contacts with free water present inside of a capsule and can be un-stabilized with the elapse of time. This would result in not only the change in the appearance such as coloration but also the decrease in the activity of an active ingredient. In addition, the gelatin capsule itself may become insoluble and soft, which may be followed by the deformation or the like. In general, the adjustment of water activity, especially the reduction thereof, was carried out by placing a drying agent such as silica gel into a container for packaging capsules so as to reduce the internal moisture of a capsule. However, it is not easy to adjust the water content in the capsule coating appropriately by this method. Especially, in the case of gelatin capsules, too much decrease in the water content might cause a crack or a crack break, leading to the damage or deformation of capsules. The normal water content or moisture content of a gelatin capsule coating is between 12 and 16% and, when it becomes below 10%, in particular, below 7–8%, cracks may happen only by slight impact. Therefore, it is desirable to decrease the content of free water inside of a capsule while maintaining the water content in the gelatin coating adequately. However, the manufacture of such capsules was difficult.

There have been reported stabilized gelatin capsules, for example, in Japanese Patent Publication (KOKAI) No. 80,930/1991, Japanese Patent Publication (KOKAI) No. 145,017/1992, Japanese Patent Publication (KOKAI) No. 159,218/1992 and the like. However, they all relate to gelatin capsules which contain a stabilizer in the gelatin coating and do not mention at all about the adjustment of water activity inside of capsules. Therefore, these literatures do not solve the problems above. Japanese Patent Publication (KOKAI) No. 24,014/1978 reported gelatin capsules containing polyvinyl pyrrolidone. However, the amount of polyvinyl pyrrolidone used per capsule is only a little and the purpose of the use thereof is the adjustment of the release rate of a drug.

Under the conditions above, the present inventors have studied intensively to establish a method for adjusting the water activity inside of a capsule (i.e., internal water activity of a capsule) appropriately, and to develop a capsule having adjusted water activity.

As a result, the present invention has been established on the basis of the finding that it is useful to add a certain substance which serves as a water activity regulating agent to the capsule content in order to adjust the internal water activity of a capsule appropriately without affecting adversely the gelatin coating.

DISCLOSURE OF THE INVENTION

The present invention provides a gelatin capsule having adjusted water activity and preserved in a closed system, which contains, packed herein, an additive(s) selected from the group consisting of carboxymethyl cellulose calcium, crosscarmellose sodium, partially gelatinized starch and polyvinyl polypyrrolidone in the proportion of 50 to 150 wt. % of the total quantity of the gelatin of the said capsule.

PREFERRED EMBODIMENT TO CARRY OUT THE INVENTION

The coating of the gelatin capsules of the present invention preferably contains as a principal component gelatin and optionally a small amount of an additive(s) for capsule coating generally used in the field of pharmaceutical industries, for example, polyethylene glycol and the like.

For purposes of the present invention, an selected additive serves as a water activity regulating agent (or a regulator) as mentioned above is packed in a capsule in the proportion of about 50 to 150 wt. %, preferably about 50 to 120 wt. %, more preferably about 50 to 100 wt. %, further more preferably about 70 to 100 wt. %, especially preferably about 75 to 90 wt. % of the total quantity of the gelatin coating.

If the amount of an additive(s) is too little, the internal water activity cannot be controlled effectively when a capsule is preserved under high temperature and high humidity, or for a long time, which possibly leads to the unstabilization or discoloration of the capsule or its content. If the amount of an additive(s) is too large, the internal water activity could be greatly decreased under a mild condition of at room temperature and a crack may happen on a gelatin capsule.

Throughout the specification, the term "water activity $(A_W)$" means a ratio of water vapor pressure (P) in a certain measurement system and that (Po) of pure water under the same temperature and pressure as those of the said measurement system, and is defined by the formula:

$$A_W = (P/Po) \times 100 (\%).$$

The water activity of each of gelatin, additive(s) and the whole capsule can be measured with any one of commercially available measuring device (e.g., Water activity $(A_W)$ measurement system of DT type, manufactured by Rotronic, Inc. (Gunze Industrial Co., Ltd.)).

The total water activity of a capsule $(A_{WT})$ is in principle the same as the mean water activity $(\underline{A}_W)$ which can be calculated from the water activity of each of the gelatin as a component of capsule coating and the additive(s) packed in the capsule in accordance with the following formula. However, they differ from each other in such a case where a shift of moisture between coating and additives occurs due to the packing of an additive(s) into a capsule.

$$\underline{A}_W = [A_W \cdot M(gelatin) + A_W \cdot M(additive)] / [M(gelatin) + M(additive)]$$

$\underline{A}_W$: mean water activity $A_W$: individual water activity

M: individual water content

Throughout the specification, when "a change in water activity" is discussed in relation to the moisture stability of capsules, the difference between the mean water activity ($\underline{A}_W$) calculated according-to the formula on the basis of the individual water activity before packing an additive(s) and the $A_{WT}$ value of a capsule calculated after packing the additive(s) is more important than the change in the absolute water activity measured for each of the gelatin and the additive(s). That is, the greater the reduction of $A_{WT}$ from $\underline{A}_W$ of a capsule, the more the water transferred from the capsule coating to an additive(s), which means that the elevation of water activity inside of the said capsule is under suppression. The capsules of the present invention may contain any of pharmacologically active and pharmaceutically acceptable drugs, as long as it does not interact with additives adversely. However, a substance which is liable to change in pharmacological activity and physicochemical characteristics such as color, particle size and the like due to the change in water activity, especially elevation thereof, is suited. Examples of such substances include antibiotics, e.g., 7β-[(Z)-2-(2-amino-4-thiazolyl)-2-hydroxyiminoacetamide]-(1,2,3-triazol-4-ylthimetylthio)-1-carba-3-cephem-4-carboxylic acid, and aspirin. Incidently, in some cases, such physicochemical change of a drug is attributable not only to the active substance but also the contaminants accompanying to the active substance.

The gelatin capsules obtained according to the present method are unexpectedly stable when preserved in a closed system, where the gelatin capsules are usually instable. Especially, a content drug(s) which otherwise is adversely affected by high water activity can be kept stably in a gelatin capsule even in a closed system at elevated temperature. At the same time, the gelatin capsule coating itself has also been stabilized. Accordingly, the present invention can contribute to the maintenance of the quality of capsules which have been considered to be subject to quality deterioration during the transportation or preservation.

Throughout the specification, the term "closed system" means a system where the distribution of outside air is blocked as completely as possible and is preferably constructed by packaging with a press-through package (PTP), alumi-pillow or the like.

The capsules of the present invention can be prepared in a conventional manner using conventional carriers, excipients and the like, except that an appropriate amount of additive(s) which serves as a water activity regulator is included. However, since an experiment revealed that additives such as cornstarch, crystalline cellulose, lactose, mannitol, sucrose and the like, which are commonly formulated into standard capsules, affect adversely on the water activity reduction (see, Test Example 2 below), it is preferable to adjust the content of these additives adequately when they are used in the preparation of capsules of the present invention. For example, a relatively slight amount of such a substance, e.g., lactose, is usable as an excipient when preparing the capsules of the present invention on condition that it does not affect adversely the reduction of water activity.

EXAMPLES

The present invention will be described in more detail in the following Examples. However, these are merely for illustration purpose and should not be construed as limiting the scope of the present invention.

In the following Examples, water content and water activity of both the coating and the content of capsules were measured under the following conditions.

Water activity:

Device: Water activity $(A_W)$ Measuring System of DT type, manufactured by Rotronic & Co. (Gunze industrial Co., Ltd.);

Specimen: 3 g; and

Temperature of jacket: 25±2° C.; 45±2° C.; or 60±2° C.

Water content:

Thermostat: SATAKE Vacuous Thermostat;

Temperature: 60±1° C.;

Vacuous Degree: 5 mmHg or below (phosphorus pentaoxide);

Desiccation time: 4 hours; and

Specimen: 0.5–1.0 g (container: diameter 1.7 cm, thickness of specimen: about 7 mm).

The measured values of water content were expressed by the proportion (%) of the weight loss (dry wt.) to the dry weight of a specimen.

Test Example 1

Influence of Temperature on the Water Activity of Gelatin

Water activity of gelatin to be used in the capsule coating was evaluated in a closed system under the conditions described above. The results obtained using gelatin alone are shown in FIG. 1.

Figure 1:
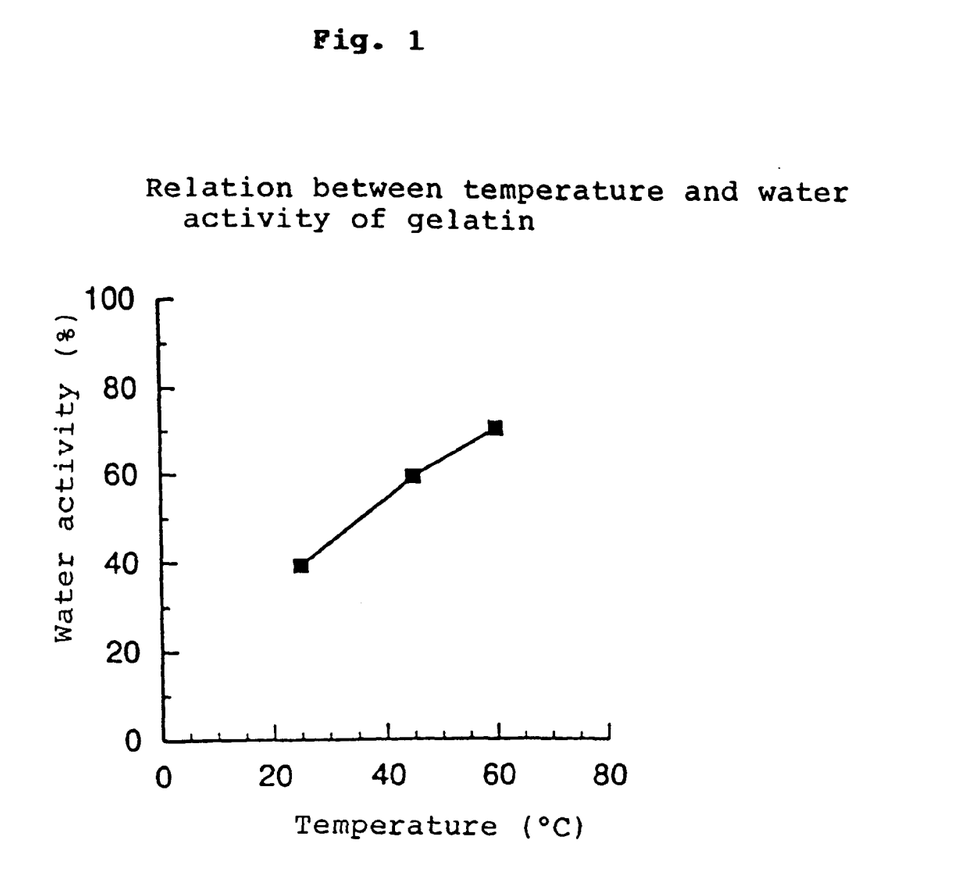
FIG. 1 is a graph showing the relation between the temperature and the water activity of gelatin which is preserved in a closed system.

From the FIG. 1, it is apparent that the water activity of gelatin increases as temperature rises, i.e., 45% at 40° C.; 55% at 50° C.; and 70% at 60° C. These results indicate that, when heated under a sealed condition, moisture evaporates from the gelatin coating of a capsule, which in turn makes the condition of inside of the capsule hyper humidity (hyper water activity).

Test Example 2

Screening of Additives Showing Reduction of Water Activity in the Presence of Gelatin Screening of a substance suited for the reduction of water activity inside of a gelatin capsule was conducted by preserving various additives alone or in a 1:1 mixture with gelatin (beads) in a closed system and determining the water activity and water content. Specifically, 1.5 g of an additive, or a mixture of 1.5 g of an additive and 1.5 of gelatin beads was placed in a vial, plugged to seal, and kept for 14 days at a constant temperature (25° C., 45° C. or 60° C.). The water activity and water content of the individual additive and gelatin were then measured. Water activity of an additive preserved in the presence of gelatin beads was measured with a device for measuring the water activity adjusted at the same temperature as storage. The water content of each additive following the preservation was measured under the conditions above after removing gelatin beads from a mixture. The results are shown in Table 1 below.

TABLE 1

(1) Water Activity

| | Additive (alone) ($A_w$) | | | Additive + gelatin ($A_{wT}$) | |
|---|---|---|---|---|---|
| | 25° C. | 45° C. | 60° C. | 45° C. | 60° C. |
| Lactose | 38.6 | 31.6 | 32.3 | 57.0(57.8) | 68.5(68.3) |
| Powdered Sugar | 11.4 | 22.4 | 26.8 | 57.4(59.2) | 67.8(70.4) |
| Mannitol | 35.4 | 24.1 | 23.1 | 57.8(59.2) | 67.2(70.2) |
| Cornstarch | 41.2 | 61.2 | 73.4 | 67.4(60.2) | 78.6(71.8) |
| Crystalline cellulose | 36.9 | 54.2 | 63.3 | 56.1(58.0) | 67.4(68.5) |
| L-HPLC | 15.1 | 30.0 | 38.2 | 45.4(51.9) | 56.3(62.2) |
| Gelatin (alone) | 39.2 | 59.3 | 70.3 | — | — |
| PVPP | 6.1 | 20.0 | 26.6 | 34.3(49.0) | 46.9(58.9) |
| Ac-Di-Sol | 3.8 | 13.3 | 21.0 | 30.1(52.2) | 41.1(62.7) |
| CMC-Ca | 2.2 | 11.4 | 20.0 | 30.9(54.8) | 42.6(60.2) |
| PCS | 16.0 | 32.4 | 39.1 | 44.4(54.8) | 56.8(65.1) |

Note:
the figure in ( ) shows the mean water activity ($A_w$) calculated from the measurements regarding gelatin and individual additive.

(2) Water Content

| | Additive (alone) | Additive + gelatin | |
|---|---|---|---|
| | 25° C. | 45° C. | 60° C. |
| Lactose | 0.74 | 0.69 | 0.50 |
| Powdered Sugar | 0.02 | 0.02 | 0.04 |
| Mannitol | 0.04 | 0.05 | 0.05 |
| Cornstarch | 12.06 | 11.93 | 11.44 |
| Crystalline cellulose | 4.36 | 4.31 | 4.31 |
| L-HPLC | 4.38 | 5.69 | 5.86 |
| Gelatin (alone) | 13.0 | — | — |
| PVPP | 4.61 | 6.83 | 6.81 |
| Ac-Di-Sol | 2.37 | 5.38 | 5.61 |
| CMC-Ca | 3.26 | 6.24 | 6.68 |
| PCS | 2.58 | 7.95 | 8.04 |

Note:
Preserving conditions: Sealed in a vial at 25° C., 45° C. or 60° C. for 14 days (1.5 g gelatin + 1.5 g additive)
L-HPC: low-substituted-hydroxypropyl cellulose
PVPP: polyvinyl polypyrrolidone
Ac-Di-Sol (Asahi Kasei/FMC Corporation)
CMC-Ca: carboxymethyl cellulose calcium
PCS: partially gelatinized starch Table 1 shows that polyvinyl polypyrrolidone (PVPP), crosscarmellose sodium (Ac-Di-Sol), carboxymethyl cellulose calcium (CMC-Ca), and partially gelatinized starch (PCS) are useful for the reduction of water activity inside of a capsule.

The Table 1 also shows that both the cornstarch and crystalline cellulose, which are often used in a standard formulation for capsules, function adversely to the reduction of water activity, which indicates that one must be careful when these additives are used in the formulation containing a drug(s) subject to influence of moisture.

Test Example 3

Stability of Aspirin in Capsules Preserved in Closed System under Heating

The test was carried out by filling a powder mixture (160 mg) of aspirin (AS) and an additive (1:1) in a hard gelatin capsule (No. 4), keeping the capsule in a closed system set by the use of BVK14 vial while heating at 60° C., and measuring the time-course of aspirin content. The results are shown in FIG. 2.

Figure 2:
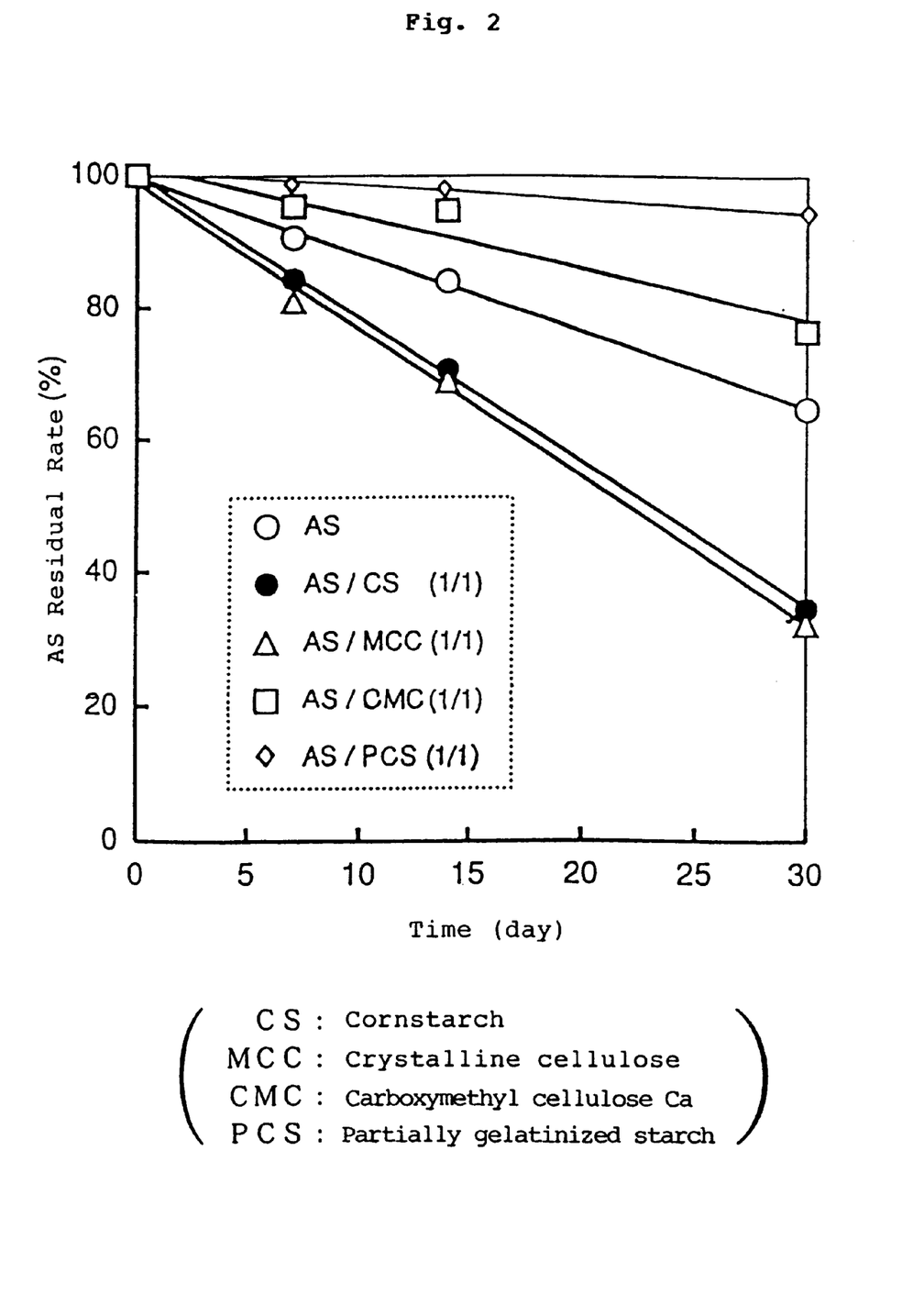
FIG. 2 is a graph showing the stability of aspirin in a capsule which contains aspirin alone or in association with an additive (CS (cornstarch); MCC (crystalline cellulose); CMS (carboxymethyl cellulose Ca); PCS (partially gelatinized starch)), when it was preserved in a closed system while heating at 60° C.

From the FIG. 2, it is clear that aspirin decomposes remarkably when preserved alone. The decomposition of aspirin is, however, inhibited in the presence of partially gelatinized starch (PCS) or carboxymethyl cellulose calcium (CMC), but accelerated in the presence of cornstarch (CS) or crystalline cellulose (MCC).

Test Example 4

Chemical Stability of Aspirin Capsules Containing Additives at Various Ratios

Gelatin capsules containing aspirin (AS) as a model drug at the ratio of 1.5 to the gelatin were prepared in the absence or the presence of an additive (PVPP, Ac-Di-Sol, CMC-Ca, PCS) at various combination ratios ((r)=0.2, 0.5, 1.0, 1.5) to the gelatin. The capsules were then subjected to an acceleration test (at 45° C. for 3 months) corresponding to a normal time-course test (at room temperature for 2 years), or a severe test (at 60° C. for 2 weeks), and the residual rate (%) of aspirin and the water activity ($A_{WT}$) of the capsule containing aspirin were measured. The results are shown in Table 2 below.

TABLE 2

| | Wt. ratio | Residual rate (%) 45° C., 3 mon. | Water activity (%) 60° C., 2 weeks |
|---|---|---|---|
| AS/GEL-Cap | (1.5)/1.0 | 84.1 (63.9) | 77.2 (75.7) |
| AS + PVPP/ GEL-Cap | (1.5, 0.2)/1.0 | 93.3 (48.0) | 83.6 (64.0) |
| | (1.5, 0.5)/1.0 | 98.0 (42.0) | 90.3 (56.2) |
| | (1.5, 1.0)/1.0 | 99.8 (35.2) | 92.8 (48.0) |
| | (1.5, 1.5)/1.0 | 100.0 (31.2) | 98.0 (44.0) |
| AS + Ac-Di-Sol/ GEL-Cap | (1.5, 0.2)/1.0 | 93.8 (46.4) | 85.5 (60.9) |
| | (1.5, 0.5)/1.0 | 100.0 (37.8) | 90.2 (53.6) |
| | (1.5, 1.0)/1.0 | 100.0 (30.6) | 97.0 (43.2) |
| | (1.5, 1.5)/1.0 | 100.0 (25.4) | 99.9 (36.8) |
| AS + CMC-Ca/ GEL-Cap | (1.5, 0.2)/1.0 | 94.2 (46.5) | 85.4 (62.1) |
| | (1.5, 0.5)/1.0 | 100.0 (37.8) | 92.1 (53.6) |
| | (1.5, 1.0)/1.0 | 100.0 (32.0) | 99.3 (44.5) |
| | (1.5, 1.5)/1.0 | 100.0 (26.2) | 100.0 (36.9) |
| AS + PCS/ GEL-Cap | (1.5, 0.2)/1.0 | 95.2 (49.1) | 83.6 (66.8) |
| | (1.5, 0.5)/1.0 | 100.0 (39.8) | 92.8 (58.4) |
| | (1.5, 1.0)/1.0 | 100.0 (39.8) | 99.8 (52.2) |
| | (1.5, 1.5)/1.0 | 100.0 (36.0) | 100.0 (48.3) |

The table 2 shows that, in the case of acceleration test (45° C., 3 months), the aspirin content decreases to about 84% in the absence of an additive, while the decrease in the aspirin content could be almost suppressed by packing any one of four kinds of additives in the proportion of about 50 wt. % or more of the gelatin coating. Further, even in the case of severe test at 60° C. for 2 weeks, it is possible to secure the aspirin residual rate of 90% or more by packing an additive in a capsule in the proportion of about 50% or more of the gelatin coating.

Test Example 5

Influence of Combination Ratio of Additive to Gelatin on Water Activity

Figure 3:
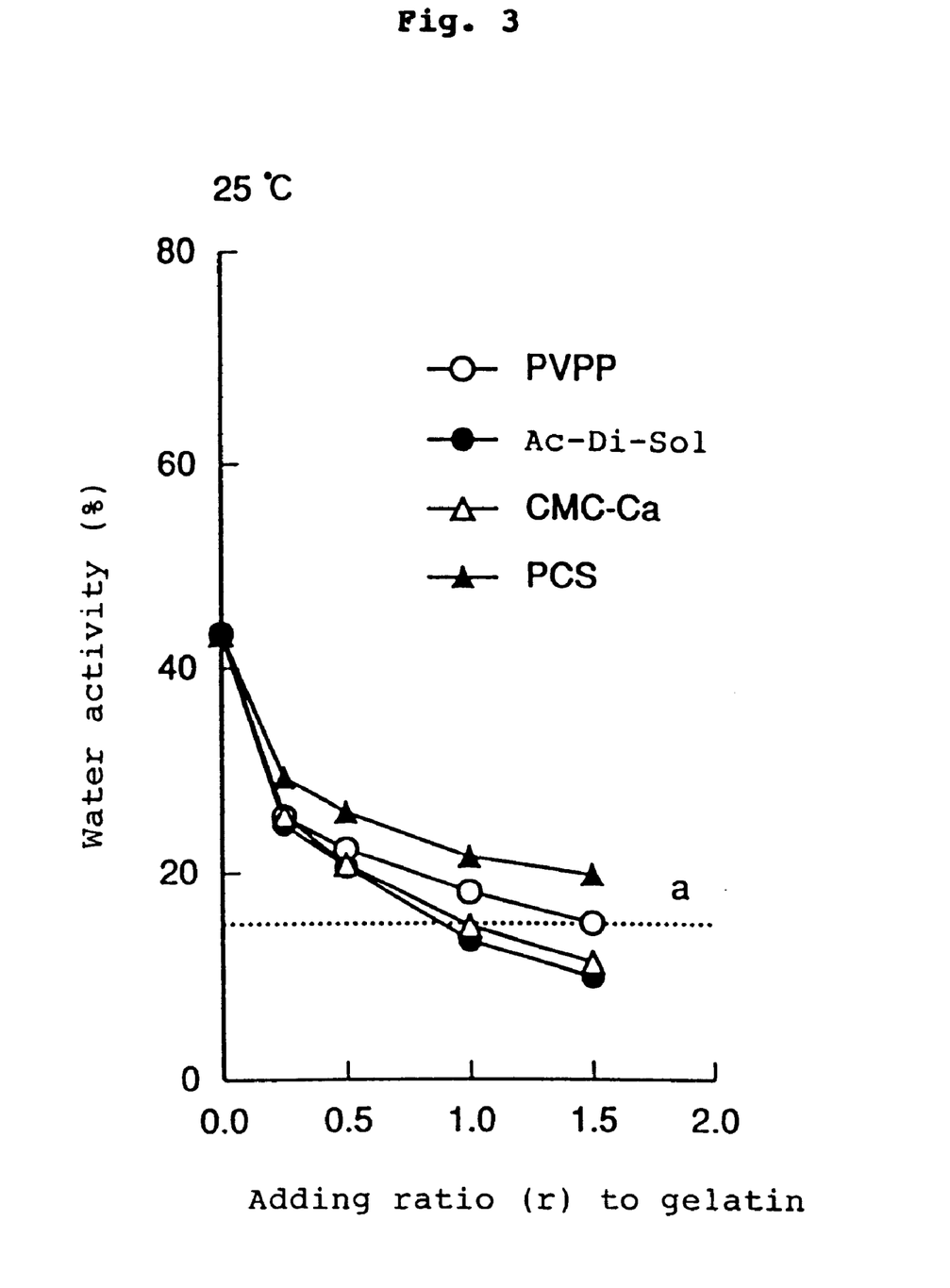
FIG. 3 is a graph showing the relation between the adding ratio of an additive to gelatin and to gelatin the water activity of gelatin beads in a mixture which contains gelatin beads and an additive (PVPP (polyvinyl polypyrrolidone); Ac-di-Sol; CMC-Ca; PCS) in various mixing ratios and was preserved in a closed system (25° C.).
Figure 4:
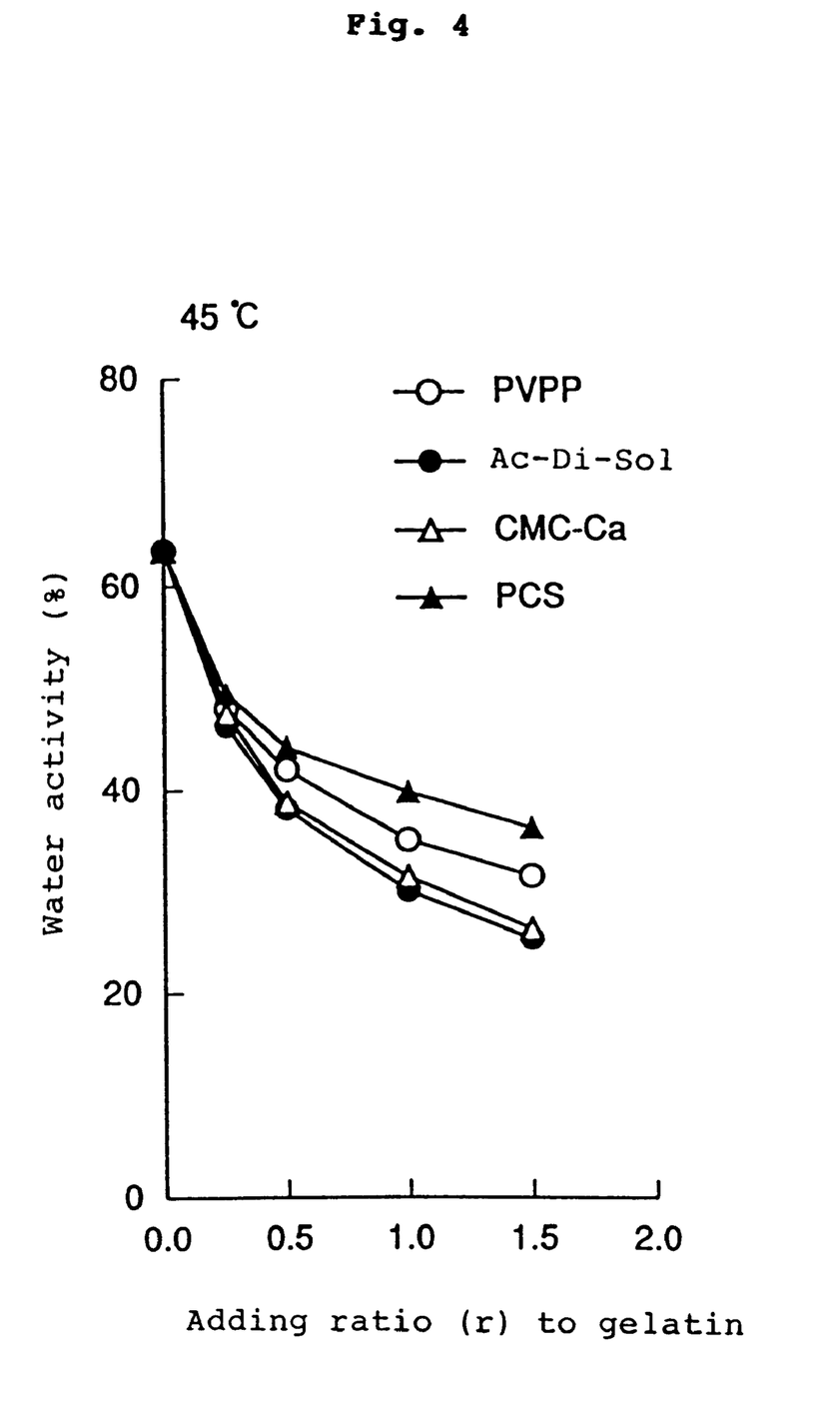
FIG. 4 is a graph showing the relation between the adding ratio of an additive to gelatin and the water activity of gelatin beads in a mixture similar to that used in FIG. 3, which was preserved in a closed system while heating (45° C.).
Figure 5:
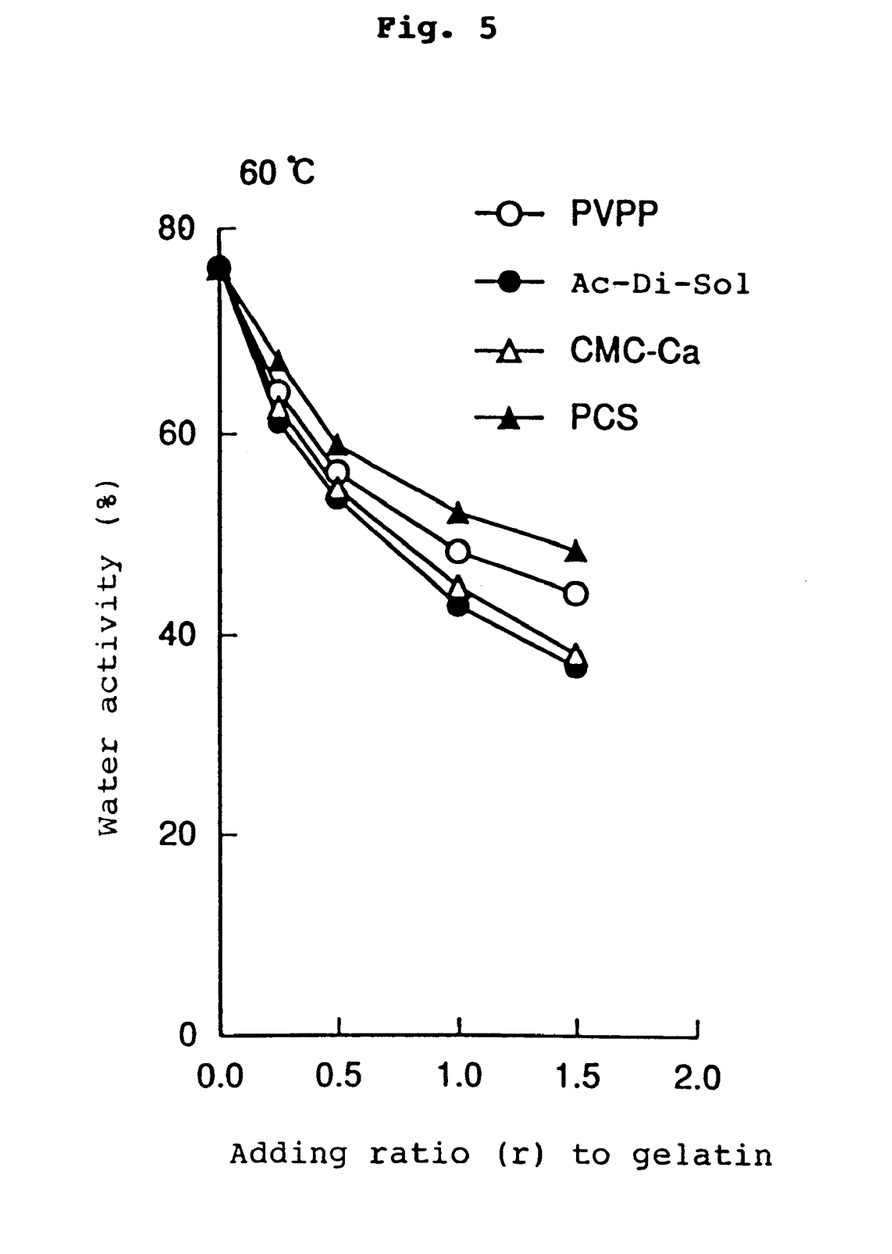
FIG. 5 is a graph showing the relation between the adding ratio of an additive to gelatin and the water activity of gelatin beads in a mixture similar to that used in FIG. 3, which was preserved in a closed system while heating (60° C.).

An additive (PVPP, Ac-Di-Sol, CMC-Ca or PCS), which proved to be effective in the reduction of water activity in Test Example 2 above, was mixed with gelatin beads at a given combination ratio (r) to obtain a mixture containing 1.5 g of gelatin beads and (1.5×(r)) g of an additive wherein (r)=0, 0.2, 0.5, 1.0, 1.5. The resulting mixture was then subjected to the measurement of water activity in the same manner as described in Test Example 2 after preserving in a sealed vial for 14 days under heating (25° C., 45° C. or 60° C.). The results obtained after preserving at 25° C., 45° C. and 60° C. are provided in FIGS. 3, 4 and 5, respectively. The FIGS. 3–5 show that the additives capable of reducing the water activity decrease the water activity of the system as a whole under any temperature condition depending on the amount used, and that the water activity of the system increases with the elevation of temperature irrespective of the kind of additive. In the figures, "a" indicates the water activity at which a crack(s) possibly happens to the number 4 capsule coating, which contains 4.6% PEG (polyethylene glycol) (cap & body OP. white, Japan Eranco). When the water activity decreases below the value at "a", the plasticity of capsule coating would decrease, leading to the increase in the probability of occurrence of crack due to breakage during transport or preservation. As is shown in FIG. 3, the preferred combination rate of an additive to capsule coating is 150% or less, at the storage temperature of 25° C.

Example 1

Capsules were prepared from the following components.

| | |
|---|---|
| Aspirin | 112.4 mg |
| CMC-Ca | 35.0 mg |
| Carplex 67 (Shionogi) | 1.7 mg |
| Magnesium stearate | 1.7 mg |
| | 150.8 mg |

The above components were mixed and the powder mixture was filled in a hard gelatin capsule of size No. 4 (40 mg) to obtain a capsule (190.8 mg).

Example 2

Capsules were prepared from the following components.

| | |
|---|---|
| Aspirin | 112.4 mg |
| CMC-Ca | 30.0 mg |
| Carplex 67 (Shionogi) | 1.5 mg |
| Magnesium stearate | 1.5 mg |
| Lactose | 9.6 mg |
| | 155.0 mg |

The above components were mixed and the powder mixture was filled in a hard gelatin capsule of size No. 4 (40 mg) to obtain a capsule (190.5 mg).

Example 3

Capsules were prepared from the following components.

| | |
|---|---|
| Aspirin | 107.0 mg |
| Ac-Di-Sol | 40.0 mg |
| Carplex 67 (Shionogi) | 1.0 mg |
| Magnesium stearate | 2.0 mg |
| Lactose | 5.0 mg |
| | 155.0 mg |

The above components were mixed and the powder mixture was filled in a hard gelatin capsule of size No. 4 (40 mg) to obtain a capsule (190.5 mg).

Example 4

Capsules were prepared from the following components.

| | |
|---|---|
| Aspirin | 102.0 mg |
| PVPP | 48.0 mg |
| Carplex 67 (Shionogi) | 1.0 mg |
| Magnesium stearate | 2.0 mg |
| Lactose | 2.0 mg |
| | 155.0 mg |

The above components were mixed and the powder mixture was filled in a hard gelatin capsule of size No. 4 (40 mg) to obtain a capsule (190.5 mg).

INDUSTRIAL UTILITY

As is apparent from the results shown in Test Examples, the gelatin capsule of the invention keeps the water activity adequately even in a closed system under heating. Accordingly, the present invention provides a gelatin capsule which is not only stable but also able to keep the content comprising a drug(s) liable to influence of moisture stably for a long term, and thereby contributing to the maintenance of the quality of the capsules.

We claim:

1. A gelatin capsule having adjusted water activity and preserved in a closed system, which contains, packed therein, an additive(s) selected from the group consisting of carboxymethyl cellulose calcium, crosscarmellose sodium, and polyvinyl polypyrrolidone in the proportion of 50 to 150 wt. % of the total quantity of the gelatin of said capsule, wherein said gelatin capsule is a pharmaceutically acceptable gelatin capsule.

2. The gelatin capsule of claim 1 wherein the additive(s) is packed in the proportion of 50 to 120 wt. % of the total quantity of the gelatin.

3. The gelatin capsule of claim 2, which is packaged in a press-through package.

4. The gelatin capsule of claim 1 wherein the additive is carboxymethyl cellulose calcium.

5. The gelatin capsule of claim 4, which is packaged in a press-through package.

6. The gelatin capsule of claim 1, which is packaged in a press-through package.

7. A method of stabilizing a pharmaceutically acceptable gelatin capsule, characterized in that an additive(s) selected from the group consisting of carboxymethyl cellulose calcium, crosscarmellose sodium, and polyvinyl polypyrrolidone in the proportion of 50 to 150 wt. % of the total quantity of the gelatin of said capsule is used as a water activity regulating agent.

8. The gelatin capsule of claim 2, wherein the additive is crosscarmellose sodium.

9. The gelatin capsule of claim 2, wherein the additive is carboxymethyl cellulose calcium.

10. The gelatin capsule of claim 1, which further contains one or more pharmaceutically active ingredients.

\* \* \* \* \*